(12) United States Patent
Gilvarg

(10) Patent No.: US 6,461,832 B2
(45) Date of Patent: Oct. 8, 2002

(54) METHOD OF DETECTING PROCARBOXYPEPTIDASE A AND CARBOXYPEPTIDASE A LEVELS IN BIOLOGICAL FLUIDS

(76) Inventor: Charles Gilvarg, 240 Hartley Ave., Princeton, NJ (US) 08540

( * ) Notice: Subject to any disclaimer, the term of this patent is extended or adjusted under 35 U.S.C. 154(b) by 0 days.

(21) Appl. No.: 09/879,413

(22) Filed: Jun. 12, 2001

(65) Prior Publication Data

US 2001/0055785 A1 Dec. 27, 2001

Related U.S. Application Data

(63) Continuation of application No. 09/402,405, filed as application No. PCT/US98/06615 on Apr. 10, 1998, now Pat. No. 6,309,850.
(60) Provisional application No. 60/055,495, filed on Aug. 12, 1997, and provisional application No. 60/041,835, filed on Apr. 10, 1997.

(51) Int. Cl.[7] ............................. C12Q 1/37; C12Q 1/00; G01N 33/53
(52) U.S. Cl. ............................. 435/24; 435/4; 435/23; 435/968; 435/963
(58) Field of Search .................. 435/24, 4, 23, 435/968, 963

(56) References Cited

U.S. PATENT DOCUMENTS

| | | | | | |
|---|---|---|---|---|---|
| 4,432,896 A | * | 2/1984 | Sugiyama et al. | ............. | 435/24 |
| 4,551,272 A | * | 11/1985 | Sugiyama et al. | ............. | 435/24 |
| 4,939,288 A | * | 7/1990 | Talley | ............. | 435/24 |
| 6,309,850 B1 | * | 10/2001 | Gilvarg | ............. | 435/24 |

FOREIGN PATENT DOCUMENTS

WO 98/45471 * 10/1998

OTHER PUBLICATIONS

Brown et al., Analytical Biochemistry, vol. 161, p. 219–225.*

* cited by examiner

*Primary Examiner*—Louise N. Leary
(74) *Attorney, Agent, or Firm*—Licata & Tyrrell P.C.

(57) ABSTRACT

Methods of enhancing sensitivity and specificity of an assay measuring enzymatic activity in a sample by measuring enzymatic activity in the sample in the presence and absence of a specific inhibitor of the enzymatic activity are provided. Methods of measuring carboxypeptidase A levels and total carboxypeptidase A levels, wherein procarboxypeptidase A is converted to carboxypeptidase A by addition of clostripain, in a biological fluid with a carboxypeptidase A substrate, specificity of which is enhanced by addition of a carboxypeptidase A specific inhibitor are also provided. In addition, methods of diagnosing acute pancreatitis by measurement of carboxypeptidase A levels and pancreatic cancer by measurement of total carboxypeptidase A levels are also provided.

3 Claims, No Drawings

METHOD OF DETECTING PROCARBOXYPEPTIDASE A AND CARBOXYPEPTIDASE A LEVELS IN BIOLOGICAL FLUIDS

INTRODUCTION

This application is a continuation of U.S. patent application Ser. No. 09/402,405 filed Oct. 4, 1999 now U.S. Pat. No. 6,309,850 which is the U.S. National Phase of PCT Application PCT/US98/06615 filed Apr. 10, 1998, which claims the benefit of priority from U.S. Provisional Application Serial Nos. 60/055,495 filed Aug. 12, 1997 and 60/041,835 filed Apr. 10, 1997.

BACKGROUND OF THE INVENTION

Determination of altered enzyme levels by measurement of enzyme activity in biological samples is used routinely by clinicians to assist in the diagnosis of a multitude of diseases or conditions wherein physical symptoms alone may not be definitive. However, the usefulness of such assays is dependent upon the specificity of the enzyme to the disease or condition and the sensitivity and selectivity of the enzymatic assay.

For example, acute pancreatitis is defined clinically as a discrete episode of symptoms caused by intrapancreatic activation of digestive enzymes. The cause of this activation is unknown; however, premature activation of zymogen to active enzymes within the pancreas results in autodigestion and inflammation of the pancreas. Symptoms include a steady, dull or boring pain in the epigastrium or left upper abdominal quadrant which is poorly localized and reaches peak intensity within fifteen minutes to one hour. The incidence of acute pancreatitis is difficult to ascertain as uniform diagnostic criteria and effort have not been applied. However, there is an urgency in accurately diagnosing acute pancreatitis to exclude other acute conditions that require different, usually surgical, management such as perforated peptic ulcer, acute cholangitis, appendicitis and mesenteric infarction. In contrast, pancreatitis is best treated through a "hands off" approach of eliminating food intake and increasing hydration.

Determination of serum amylase activity is the test most frequently used for the diagnosis of acute pancreatitis. The frequent use of this test undoubtedly stems from the ease in obtaining substrate and performing the spectrophotometric analysis. In addition, the cost is significantly less as compared to an ultrasound or CT scan. However, results from this assay are difficult to interpret with any certainty due to the extensive distribution and background levels of amylase throughout the body. Pancreatic amylase only accounts for approximately 40% of the amylase found in serum. In fact, many individuals experience hyperamylasis for reasons unrelated to pancreatic pathology such as salivary diseases, gut diseases, liver diseases and other conditions such as renal failure, thermal burns, alcoholism, postoperative state, ketoacidosis, fallopian or ovarian cysts, pneumonia, anorexia and abdominal aortic aneurysm. (Pieper-Bigelow et al. (1990) *Gastroenterol. Clin. North Am.* 19:793–810).

Sensitivity of the amylase test is also suspect, in part, because of the short half-life of the enzyme relative to others produced in the pancreas. With a half-life of only two hours, amylase is the first enzyme to return to normal levels (Ventrucci et al. (1987) *Pancreas* 2:506–509) resulting in a sensitivity of only 33% two days after an initial bout of pancreatitis (Winslet et al. (1992) *Gut* 33:982–986).

Further, even in cases where pancreatic disease is known to be present, there is no correlation between the severity of pancreatitis and the level of serum amylase.

Accordingly, a number of digestive enzymes produced by the pancreas have been considered as possible alternatives to amylase.

Carboxypeptidase A (CPA) is a digestive enzyme synthesized exclusively by the pancreas as a zymogen precursor, procarboxypeptidase A (PCPA). Significant levels of CPA have been detected in serum of those suffering from acute pancreatitis, while healthy individuals have little (Roth, M. and Rohner, A. (1983) *Clin. Chim. Acta.* 135:65–71; Kazmierczak, S. C. and Van Lente, F. (1989) *Clin. Chem.* 35:251–255) to no (Peterson et al. (1982) *Anal. Biochem.* 125:420–426; Brown et al. (1987) *Anal. Biochem.* 161:219–225) detectable amounts of the enzyme. Several substrates and a variety of assay procedures have been proposed for the determination of the pancreatic enzyme CPA. Such assays include UV spectrophotometry to directly monitor the cleavage of the peptide bond, and calorimetric and fluorometric methods to measure the amino acid released from the C-terminus. (Bergmeyer, H. U., Ed. (1974) *Methods of Enzymatic Analysis*, Vol. 2, 2nd ed., Academic Press, New York; Roth, M. and Rohner, A. (1983) *Clin. Chim. Acta* 135:65–71). More frequently used substrates include N-benzyloxycarbonyl-glycyl-L-phenylalanine (Z-Gly-Phe) and hippuryl-phenylalanine (Bz-Gly-L-Phe). An assay involving the determination of the α-naphthol released from the N-terminal blocking group in naphthoxycarbonyl-phenylalanine has also been disclosed. (Ravin, H. A. and Seligman, A. M. (1951) *J. Biol. Chem.* 190:391–402). In addition, a spectrophotometric assay employing N-(2-furanacryloyl)-L-Phe-L-Phe (FAPP) has been reported. (Peterson et al. (1982) *Anal. Biochem.* 125:420–426). However, while the FAPP substrate had the best kinetic constants of any CPA substrate to date, its modest change in absorbance at 330 nm ($\epsilon=2000$) and the high initial absorbance at that wavelength ($\epsilon=9350$) significantly reduce the sensitivity and precision of this assay.

A new class of synthetic peptides suitable for assaying peptidase activity was described by Kingsbury et al. (1984) *Proc. Nat'l Acad. Sci. USA* 81:4573–4576. These peptides contain amino acid mimetics with nucleophilic substitutions at the α-carbon of glycine residues. The amino acid mimetics are stable when the nitrogen lone pair electrons are delocalized, as they are in a peptide bond, and release of the amino acid mimetic results in its decomposition to generate the nucleophilic substituent. If the substituent is linked to the glycine residue through sulfur, decomposition yields a compound with a free sulfhydryl group. Its appearance can be monitored spectrophotometrically in the presence of Ellman's reagent which reacts rapidly and quantitatively with free sulfhydryl groups to form a highly colored anionic species that absorbs at 412 nm. (Ellman, G. L. (1959) *Arch. Biochem. Biophys.* 82:70–77). An assay for measuring CPA in serum with the N-blocked phenylalanine substrate, N-acetyl-phenylalanyl-L-3-thiaphenylalanine was developed. (Brown et al. (1987) *Analytical Biochemistry* 161:219–225). However, use of an assay measuring CPA activity to diagnose acute pancreatitis has been debated.

Using p-OH Bz Gly Phe as a CPA substrate, Kazmierczak and Van Lente carried out an extensive study comparing CPA, amylase and lipase levels as indicators of acute pancreatitis. A major difficulty for CPA was their finding that patients with renal insufficiency, but without pancreatitis, appeared to have elevated levels of the enzyme. Kazmierczak and Van Lente also found the diagnostic sensitivity of the three assays to be comparable at cutoff values of 3 (23 µg/L), 185 and 300 U/L, respectively. They concluded that automated analysis for CPA activity, even in the absence of interferences, does not add to the diagnostic information provided by the widely available assays for amylase and lipase activity. (Kazmierczak, S. C. and Van Lente, F. (1989) *Clin. Chem.* 35(2):251-5). High levels of CPA were also reported to be present in normal serum by Roth, M. and Rohner, A. (1983) *Clin. Chim Acta* 135:65–71. Both groups found the average value of putative CPA in normal sera to be approximately 3.9 µg/L.

Pancreatic cancer is even more difficult to diagnose than acute pancreatitis, resulting in an abysmal mortality rate since individuals frequently seek treatment only after the disease has reached advanced stages which are accompanied by pain, weight loss and jaundice. The cancer is rarely diagnosed in its initial stages, in part because no cost-effective, non-invasive diagnostic test exists to date. While ultrasonography, CT scans and endoscopic retrograde cholangiopancreatography can confirm the presence of pancreatic cancer, these procedures are too expensive to use for general screening and are normally not applied until too late. Attempts to discover a marker for pancreatic cancer have been hindered by the fact that little is known about risk factors which would predispose individuals to the cancer. However, a number of individuals with pancreatic cancer have been reported to demonstrate high PCPA serum levels with normal amounts of CPA. Accordingly, determination of elevated levels of PCPA may serve as an early screen for this disease which has the lowest survival rate of any cancer. Like CPA, however, attempts to measure PCPA in serum have produced conflicting results.

Trypsin can fully activate PCPA in a concentration-dependent manner. It has been reported that 2 mg of trypsin per ml of serum can produce maximum activity of CPA in thirty minutes, although half as much trypsin required 120 hours. Amounts less than 0.5 mg per ml showed no detectable activation. (Peterson, L. M. and Holmquist, B. (1983) *Biochemistry* 22:3077–3082). These values are different from other studies, however, wherein maximum activity was obtained with 1 mg trypsin per ml of serum (Brown, K. S. Senior Thesis, Princeton University 1986).

Accordingly, there is a need for more sensitive and definitive enzymatic assays to diagnose diseases such as acute pancreatitis and pancreatic cancer in patients.

SUMMARY OF THE INVENTION

An object of the present invention is to provide a method of enhancing the sensitivity and specificity of an assay measuring enzymatic activity in a sample which comprises measuring enzymatic activity in the sample in the presence and absence of a specific inhibitor of the enzymatic activity.

Another object of the present invention is to provide a method of measuring carboxypeptidase A levels in biological fluids which comprises contacting a biological fluid with a carboxypeptidase A substrate in the presence and absence of a carboxypeptidase A specific inhibitor and measuring changes in optical density resulting from hydrolysis of the carboxypeptidase A substrate by carboxypeptidase A in the presence and absence of the carboxypeptidase A specific inhibitor.

Another object of the present invention is to provide a method of diagnosing acute pancreatitis in a patient comprising detecting elevated levels of carboxypeptidase A in a biological fluid of a patient using a carboxypeptidase A substrate, the specificity of which is enhanced by addition of a carboxypeptidase A specific inhibitor.

Yet another object of the present invention is to provide a method of measuring total carboxypeptidase A levels, including both carboxypeptidase A and procarboxypeptidase A in a biological fluid which comprises converting any procarboxypeptidase A in the biological fluid to carboxypeptidase A by addition of clostripain; contacting the biological fluid with a carboxypeptidase A substrate in the presence and absence of a carboxypeptidase A specific inhibitor; and measuring changes in optical density resulting from hydrolysis of the carboxypeptidase A substrate by carboxypeptidase A in the presence and absence of the carboxypeptidase A specific inhibitor.

Yet another object of the present invention is to provide a method of diagnosing pancreatic cancer in a patient which comprises detecting elevated levels of total carboxypeptidase A in a biological fluid of a patient by converting any procarboxypeptidase A in the biological fluid to carboxypeptidase A by addition of clostripain and contacting the biological fluid with a carboxypeptidase A substrate, the specificity of which is enhanced by addition of a carboxypeptidase A specific inhibitor, and contrasting the total carboxypeptidase level with an amount of carboxypeptidase A in the sample determined in the absence of clostripain so that elevated levels of procarboxypeptidase A indicative of early stage pancreatic cancer can be determined.

DETAILED DESCRIPTION OF THE INVENTION

It has now been found that the sensitivity and specificity of enzymatic assays can be enhanced by utilization of blanks containing an inhibitor specific to the enzyme. For example, the pancreatic enzyme carboxypeptidase A was first characterized by Anson in 1937. (Anson, M. L. (1937) *J. Gen. Physiol.* 20:663). N-acetyl-phenylalanyl-L-3-thiaphenylalanine is a specific substrate for carboxypeptidase A (CPA) and has been proposed as a replacement for the amylase assay in diagnosing pancreatitis. (Brown et al. (1987) *Analytical Biochemistry* 161:219–225). However, the extraneous optical density changes associated with its application to serum determinations limited sensitivity and reproducibility of this assay. Further, the question of high CPA baseline levels in the serum of healthy subjects has been raised which is critical to diagnostic use of the assay as it directly reflects upon the sensitivity in which a particular assay is capable of assessing pancreatic pathology.

It has now been demonstrated that the sensitivity and specificity of an assay measuring levels of carboxypeptidase A (CPA) in a biological fluid by addition of a CPA substrate is enhanced by utilization of a blank containing a CPA specific inhibitor. In a preferred embodiment of this CPA assay, the biological fluid comprises plasma or serum. However, it is believed that this assay could also be used to determine CPA levels in other biological fluids such as urine. Addition of CPA specific inhibitors α-benzylsuccinic acid or potato CPA inhibitor (CPI) to CPA assays with the substrate N-acetyl-phenylalanyl-L-3-thiaphenylalanine (NAcPSP) was found to correct for all extraneous changes in optical density (O.D.) resulting from decomposition of the substrate or reagents. By addition of these specific inhibitors to the blank, it is now possible to specifically measure the changes in optical density resulting from the low amount of CPA, i.e., 0.3 µg/L, in normal human serum. Accordingly, an assay measuring enzymatic hydrolysis of a CPA substrate, preferably NAcPSP in the presence and absence of a CPA specific inhibitor, can now be used to reproducibly detect CPA levels in biological fluids and in diagnosing acute pancreatitis.

In this assay, hydrolysis of the CPA substrate is measured using Ellman's reagent. Ellman's reagent reacts rapidly and quantitatively with free sulfhydryl groups to form a highly colored anionic species that absorbs at 412 nm. (Ellman, G. L. (1959) *Arch. Biochem. Biophys.* 82:70–77). However, neither the substrate nor Ellman's reagent used to measure hydrolysis of the substrate are completely stable compounds. Accordingly, decomposition of these compounds results in an increase in O.D. during the assay. In addition, the half-Ellman which is liberated by the interaction of the Ellman's reagent with serum albumin is subject to reoxidation which causes a decrease in O.D. These effects are quite modest for ordinary analytical purposes. For example, substrate breakdown is 0.63 percent per hour at 37° C. However, the O.D. increases attributable to the minute amount of CPA in the serum of healthy individuals is so small that these ancillary O.D. changes can be dominating. Further, a blank containing Ellman's reagent and substrate only does not compensate for the reoxidation. Alternatively, a blank containing serum and Ellman's reagent does not compensate for substrate breakdown. In the assay of the present invention, however, wherein a specific CPA inhibitor is added to the blank, all extraneous O.D. changes are corrected. In the manual assay described below, the CPA specific inhibitor is prepared in a concentrated solution so that only a very small volume is required thus rendering any pipetting error in dispensing it to have an inappreciable effect on concentration relationships.

Accordingly, the present invention provides a diagnostic assay for pancreatitis by measuring levels of CPA in a biological fluid such as serum using a CPA substrate, preferably NAcPSP. As will be obvious to those of skill in the art, however, CPA substrates with a similar Michaelis constant, Vmax, and extinction coefficient to NAcPSP can also be used. The specificity of the substrate for the enzyme is enhanced by addition of a CPA specific inhibitor to the blank. For example, FAPP has been disclosed to produce such modest changes in absorbance that the sensitivity and precision of an assay measuring CPA in serum is significantly reduced. However, addition of a CPA specific inhibitor to the blank of this assay increased the sensitivity and precision such that FAPP is a useful substrate for determination of CPA levels in serum with the method of the present invention. Examples of CPA specific inhibitors which can be used include, but are not limited to, α-benzylsuccinic acid ($K_i$=1 μM) and CPI. Monoclonal antibodies raised against the enzyme in accordance with well known methods can also be used as specific inhibitors in the assay. By adding a specific enzyme inhibitor to the assay blank, only optical density changes attributable to enzymatic cleavage of the substrate are measured. Assays are performed in pairs with the inclusion of a sufficient concentration of inhibitor in the second cuvette to eliminate at least 99 percent of any CPA activity and to correct for extraneous O.D. changes in normal serum thus making it possible to accurately detect CPA levels in serum of healthy adults. Assays can be performed by a manual method or in a Cobas Bio centrifugal analyzer (Roche Diagnostics Systems, Branchburg, N.J.) at 37° C.

Stability of CPA activity during the time period for the assay of the present invention was confirmed. In these experiments, sera from two individuals was assayed and monitored spectrophotometrically every hour over a period of six hours. Absorbance increased in a linear fashion for both samples, thus indicating that CPA activity was in fact being monitored and that it was stable at 37° C. for this time period, which is actually twice as long as the standard assay. These studies also indicate that, while incubation for three hours is preferred, activity after only a one hour incubation period provides an accurate estimate of CPA activity for diagnostic purposes since CPA activity, on average, is linear throughout the incubation period. Further, experiments in serum from four different individuals demonstrated a linear increase in ΔOD which correlated with serum concentrations.

Specificity of the assay for CPA and not PCPA was also confirmed. In these experiments, three different samples were tested for CPA activity using either α-benzylsuccinic acid or CPI, an inhibitor that does not bind to PCPA. Both inhibitors were added at concentrations sufficient to eliminate at least 99% of all CPA activity. In two of the samples from healthy individuals, CPA activity was approximately equivalent with the two inhibitors. The third sample, which was known to have approximately 250 times more PCPA than CPA, also yielded similar results with the two inhibitors.

Reproducibility of the assay of the present invention was determined in sera from two individuals by performing numerous assays on specific serum samples. Analysis of three samples from each individual revealed that CPA activity measurements were reproducible for both a given serum and among different samples for a given individual. Results from these experiments are depicted in Table 1. Enzyme activity is expressed in U/L.

TABLE 1

|  | Trials | Mean | ±2S |
|---|---|---|---|
| Serum #1 |  |  |  |
| set 1 | 10 | 0.098 | 0.030 |
| set 2 | 11 | 0.098 | 0.037 |
| set 3 | 9 | 0.109 | 0.040 |
| Serum #2 |  |  |  |
| set 1 | 9 | 0.058 | 0.022 |
| set 2 | 9 | 0.046 | 0.014 |
| set 3 | 14 | 0.042 | 0.024 |

Variability of CPA activity measurements for a single sample is believed to be largely attributable to the reproducibility of the spectrophotometric determination in view of the exceedingly high levels of sensitivity at which CPA is being measured. Mean CPA activity varied somewhat among samples drawn at different times from a given individual, although all sets overlap within error demonstrating that a healthy individual does not experience wide fluctuations in serum CPA levels.

Having established the selectivity and reproducibility of this assay, a larger study was performed on 108 samples of plasma collected from healthy blood donors. Using the standard assay described in Example 2 with 0.1 ml serum per ml of solution, the CPA level of each sample was determined. CPA activities were distributed somewhat asymmetrically although they approximated a normal distribution with a mean of 0.068±0.055 U/L (X±2S) and a median of 0.064 U/L.

CPA activities in males and females, analyzed independently, had similar distributions. Of the 108 samples, 62 were taken from males with an in-class mean of 0.071±0.057 U/L (X±2S) and median of 0.068, while 46 females had a mean of 0.063±0.050 U/L (X±2S) and a median of 0.057 U/L. Further analysis of the data revealed no correlation between CPA levels and age of the donors (ranging from 21 to 79 years).

The baseline of the assay of the present invention is approximately 58 fold less than that reported by Kazmierczak and Van Lente as a cutoff (Kazmierczak, S. C. and Van Lente, F. (1989) *Clin. Chem.* 35(2):251-5). Thus, the assay of the present invention is much more sensitive than the CPA assay taught by Kazmierczak and Van Lente to probably not be "warranted" in diagnosing pancreatitis. Further, elevated levels of CPA observed by Kazmierczak and Van Lente in patients suffering from renal insufficiency have recently been found to be attributable to a several fold elevation in the proenzyme without any accompanying appearance of detectable CPA. Therefore, contrary to teachings in the prior art, the CPA assay of the present invention is useful in diagnosing pancreatitis.

A number of patients were tested with this assay to assess levels of CPA activity during illness. Two main groups were studied: individuals diagnosed with pancreatitis and patients with nonpancreatic diseases. Tests on pancreatic serum were conducted with the automated assay described in Example 2. Elevations in serum CPA concentrations were observed in seven selected pancreatics with values as high as 1000 times above baseline. Tests on serum from patients with nonpancreatic conditions uncovered an enormous variety of disease states with elevated amylase but normal CPA levels.

Accordingly, patients exhibiting symptoms of acute pancreatitis can be diagnosed quickly and easily using the assay of the present invention to detect elevated levels of CPA. Using this assay, normal CPA activities have been determined to have a range of 0.068±0.083 U/L (X±3SD). Accordingly, serum levels of CPA greater than 0.20 U/L are considered elevated and are indicative of pancreatitis.

As will be obvious to those of skill in the art upon this disclosure, average CPA levels in other biological fluids from healthy control populations such as plasma, saliva or urine can be routinely determined in accordance with these teachings and elevated CPA levels in these biological fluids can also be indicative of pancreatitis.

Further, while the focus of these experiments was upon enhancing the CPA assay, the addition of a specific inhibitor to the blank of an enzymatic assay can be used to enhance the accuracy and sensitivity of any enzyme assay. Various specific inhibitors for selected enzymes are known in the art and can be routinely added to blanks of assays for the selected enzymes in accordance with the teachings herein. Further, monoclonal antibodies against a selected enzyme which are also useful as specific inhibitor in the method of the present invention can be raised in accordance with well known techniques. Accordingly, the present invention provides a method for enhancing the sensitivity and specificity of any assay measuring enzymatic activity in a sample wherein enzymatic activity in the sample is measured in the presence and absence of a specific inhibitor of the enzymatic activity.

It has also been found that the CPA assay of the present invention can be modified to measure both CPA and PCPA, referred to herein as "total CPA", in a biological fluid. Several enzymes have been suggested for use in measuring levels of total CPA activity including bovine trypsin, subtilisin and urokinase, with bovine trypsin being preferred. (Peterson, L. M. and Holmquist, B. (1983) *Biochemistry* 22:3077–3082). However, attempts to optimize PCPA activation by trypsin by addition of combined reagents and soybean trypsin inhibitors after a short incubation indicate that trypsin activated serum does not reflect actual PCPA levels due to tryptic-induced degradation of CPA.

In the present invention, the protease clostripain was added to activate any PCPA in the biological fluid so that total CPA could be measured. Tests with sera from four healthy individuals and one with pancreatitis indicated that, unlike trypsin, supramaximal clostripain concentrations resulted in only slight CPA activity losses. Further, CPA activities after clostripain activation were significantly higher than the maximum values that could be obtained when using trypsin.

Sixty-six samples previously tested for CPA activity were analyzed for total CPA activity following clostripain activation. Of these, two samples had exceedingly high levels of PCPA and were not analyzed further since they fell well outside the range of "normal" based upon calculations with the other samples. Overall, males (37) had a mean value for total CPA activity of 1.50±0.82 U/L (X±2S) while females (27) had a distribution of 1.50±1.04 U/L (X±2S).

Serum from patients with pancreatic cancer at various stages and patients with related conditions were analyzed for total CPA concentrations by the assay of the present invention wherein clostripain was first added to convert any PCPA to CPA. A detailed description of activation by clostripain is provided in Example 7. Data from these experiments are shown in Table 2.

TABLE 2

CPA and total CPA activity in patient with pancreatic cancer and related diseases

| Patient | CPA (U/L) | Total CPA (U/L) | Ratio | Diagnosis |
|---|---|---|---|---|
| FLC | 0.061 | 43.9 | 720 | adenocarcinoma of head |
| TMa | 0.008 | 6.99 | 874 | adenocarcinoma (lymphatics) |
| S | 0.126 | 5.61 | 45 | adenocarcinoma |
| SSa | 0.090 | 4.97 | 55 | islet cell tumor |
| SSb | 0.038 | 3.27 | 86 | adenocarcinorna |
| VC | 0.049 | 3.19 | 65 | adenocarcinoma; head removed |
| RD | — | 3.06 | — | duodenal tumor with obstructed duct |
| TMb | 0.037 | 1.70 | 46 | cancer of the ampulla |
| SG | 0.046 | 1.14 | 25 | pancreatic tail tumor with duct polyps |
| GT | 0.034 | 0.82 | 24 | advanced, unresectable cancer |
| DJ | 0.088 | 0.45 | 5 | advanced adenocarcinoma |

While cancer patients exhibited normal CPA levels, total CPA concentrations were well above normal for several individuals. Those patients who demonstrated the highest PCPA levels generally suffered from resectable, early stage cancer. In contrast, individuals with advanced stages of cancer (GT and DJ) had very low PCPA levels, with serum from DJ containing less PCPA (0.36 U/L) than any individual in the healthy population. Accordingly, elevated levels of PCPA determined by measuring total CPA using the assay of the present invention is believed to be useful as a marker in the diagnosis of early stage pancreatic cancer.

The following nonlimiting examples are provided to further illustrate the instant invention.

EXAMPLES

Example 1

Materials

N-acetyl-phenylalanyl-3-thiaphenylalanine (NAcPSP) was obtained from Peptides International (Louisville, Ky.)

and stored at room temperature in a desiccator. Bovine trypsin, clostripain, subtilisin, urokinase, Nα-benzoyl-L-arginine p-nitroanilide (BAPNA), soybean trypsin inhibitor (STI), and bovine serum albumin were all obtained from Sigma Chemical Co. (St. Louis, Mo.) and stored over desiccant at 4° C. Ellman's reagent [5,5'-dithio-bis(2-nitrobenzoic acid)],DL-benzylsuccinic acid, and N-(3-[2-furyl]acryloyl)-phe-phe (FAPP) were also purchased from Sigma and stored at room temperature. Carboxypeptidase Potato Inhibitor (CPI) and dithiothreitol (Cleland's Reagent) were obtained from Calbiochem (San Diego, Calif.) and stored over a desiccant at 4° C. All other chemicals were of analytical grade.

Solutions of NAcPSP, FAPP, Ellman's reagent, α-benzylsuccinic acid, clostripain and bovine CPA were stored at −20° C. All other solutions were made on the day of the experiment and kept at 0° C.

Blood and plasma used to assess baseline CPA and PCPA levels was collected in three sets from blood donors at New York Hospital. Other blood samples were obtained from either the NYU Hospital or the McCosh Clinic at Princeton University. All samples were stored at −20° C.

Pancreatic juice was obtained from the externalized pancreatic duct in an otherwise healthy individual and stored at −20° C.

Example 2

Standard Assay for Measuring CPA Activity in Human Serum

CPA activity was determined by applying the substrate NAcPSP to a solution containing Ellman's reagent and serum and subsequently monitoring the production of the half Ellman's anion at 412 nm spectrophotometrically. This assay employed the following reactants at the indicated final concentrations: human serum (usually 0.1 ml per ml total solution); Ellman's reagent (0.5 mM); Tris buffer, pH 7.5, (0.2 M); NaCl (0.5 M); and NAcPSP (0.4 mM). Serum concentrations ranging from 0.003 to 0.15 ml of total solution were also applied. The total volume of the reactants was three ml.

The addition of Ellman's reagent to the serum was followed by a five minute incubation at 22° C., which allowed free sulfhydryl groups in the serum to react to completion with Ellman's reagent. After the addition of NAcPSP, one ml of this mixture was dispensed into each of two plastic cuvettes with one-cm path lengths. One of these cuvettes (referred to herein as the blank) contained one microliter of a CPA inhibitor (0.4 M in the case of benzylsuccinate) and the other cuvette (referred to herein as the test) contained a microliter of water. The cuvettes were then sealed and incubated at 37° C. Absorbance was monitored every hour or hour and a half for a total of three hours with a Zeiss model PM6 spectrophotometer (Thornwood, N.Y.).

This determination of CPA levels was based upon the difference in absorbance between the blank and the test cuvettes for a given sample and presented as units of activity per liter of serum in accordance with the following calculation. A unit is defined as one micromole of half-Ellman's anion produced per minute. Since Ellman's anion has a molar extinction coefficient of 13,600 L/Mol-cm at 412 nm, the production of one μmole per ml of solution results in an increase in absorbance of 13.6.

$1 \ U/L \approx (1 \ \mu mole/min)/L$ serum $\approx (13.6 \ \Delta OD/min)/L$ serum $\approx (0.00136 \ \Delta OD/min)/0.1$ ml serum After 3 hours, the change in absorbance is 0.245 relative to a blank with no CPA activity for 1 U/L with the standard assay.

An automated assay using the Cobas Bio analyzer was also performed wherein a first set of determinations was made without the inhibitor. A second set was then made wherein the substrate solution contained the inhibitor. In the automated assay, the analyzer was set to provide for a five minute reaction time of the Ellman Reagent with the serum after which substrate was added and optical density determinations were made every 10 seconds for five minutes at a wavelength of 412 nm.

Example 3

Determination of Kinetic Constant of CPA Substrates

Kinetic constants of serum CPA were determined for NAcPSP by utilizing the standard procedure and modifying the concentration of substrate within the range of 0.1 to 0.8 mM. Experiments were also performed using bovine CPA, pancreatic juice, and pseudocyst fluid, with each applied in concentrations high enough so that initial velocity calculations could be made following change in absorbance for two minutes. All CPA sources were additionally tested with FAPP in order to obtain values for Km and relative velocities. Assays of FAPP hydrolysis involved the addition of enzymes to solutions containing FAPP (0.02 to 0.2 mM) in a buffer of 50 mM Tris (pH 7.5) and 0.45 M NaCl. The reaction was followed at 330 nm using a Zeiss model PM6 spectrophotometer. At this wavelength the substrate has a high initial absorbance ($\epsilon$=9350) which declines as the reaction proceeds ($\Delta\epsilon$=2000). (Peterson et al. (1982) *Anal. Biochem.* 125:420–426).

Lineweaver-Burke analysis was used to evaluate Michaelis constants for CPA with the two substrates. Independent confirmation of these constants for FAPP were made using competitive inhibition analysis. NAcPSP hydrolysis was allowed to proceed following introduction of CPA for one minute, at which point a small, concentrated volume of FAPP was added to the solution. The change in velocity which resulted was used to calculate a $K_i$ of FAPP against NAcPSP.

Example 4

Comparison of CPA Inhibitors

Solutions of α-benzylsuccinic acid with a reported $K_i$ of 1 μM and 1.6 μM (Byers, L. D. and Wolfenden, R. (1973) *Biochemistry* 12:2070–2078; Peterson et al. (1976) *Biochemistry* 15:2501–2508), and Carboxypeptidase Potato Inhibitor (CPI), with a reported $K_i$ of 5 nM (Hass, G. M. and Ryan, C. A. (1980) *Biochem. Biophys. Res. Commun.* 97:1481–1486) were prepared such that each solution had similar efficiency at eliminating CPA activity as determined by their ability to arrest the activity of 50 ng bovine CPA assayed using the standard procedure described in Example 2. Final concentrations of the 1 μl addition of the two solutions were 0.4 M for α-benzylsuccinic acid and 1.4 mM for CPI. To compare their effectiveness in eliminating serum CPA activity, an identical amount of each inhibitor solution was added to two sets of three different serum samples, which were assayed by the standard procedure.

Further tests were also performed with α-benzylsuccinic acid at different concentrations. In these tests, a higher volume of inhibitor solution applied to the blank cuvette was always paralleled with an identical increase in water added to the test cuvette.

Example 5

Bovine Trypsin Activity in Normal and Serum Titrated Solutions

Activities of bovine trypsin solutions were assessed by monitoring the hydrolysis of N-benzoyl-Arg-p-nitroanilide (BAPNA) at 406 nm with a Zeiss model PM6 spectrophotometer. BAPNA was used at a final concentration of 0.2 mM in 10 mM Tris buffer (pH 8.0). Following the addition of specified amounts of trypsin to the substrate solution, absorbance was followed over a period of two minutes with readings taken every 15 seconds. The procedure was used to determine activity of pancreatic juice, human serum, human serum spiked with bovine trypsin, and clostripain.

Slight modifications of this protocol were made when testing for trypsin activity in the presence of serum. NaCl, Tris buffer (pH 8.0), and BAPNA at a final concentration of 0.5 M, 6 mM, and 0.2 mM, respectively, were added to a plastic cuvette containing 0.025 ml of serum for a total volume of 1 ml. A concentrated trypsin solution (5 mg trypsin/ml 10 mM Tris buffer, pH 8.0) was added to the mixture in amounts ranging from 0.4 to 4 mg trypsin per ml serum. Absorbance was monitored spectrophotometrically at 406 nm every fifteen seconds for three minutes.

Example 6

Activation of PCPA in Human Serum with Trypsin

Activation of PCPA with bovine trypsin was performed in accordance with methods described by Peterson, L. M. and Holmquist, B. (1983) *Biochemistry* 22:3077–3082. Bovine trypsin was dissolved in 10 mM Tris buffer (pH 8.0) and added to provide a final concentration of 0.5 to 6 mg/ml serum. Following a thirty minute incubation at 37° C., total CPA activity was determined using the standard assay described in Example 2. Similar experiments were performed wherein PCPA was activated with subtilisin and urokinase.

Alternatively, trypsin was added after all other reagents had been added to the serum to provide substrate enhanced protection for the CPA. More specifically, trypsin was added after the addition of NAcPSP to the serum containing the Ellman's reagent. The mixture was then incubated for five minutes at 37° C. at which time soybean trypsin inhibitor (STI) was added in sufficient quantity (approximately 2 mg STI/5 mg trypsin) to eliminate all bovine trypsin activity. Following this step, the solution was separated into two cuvettes as described in Example 2 and monitored at 412 nm for 3 hours with a Zeiss model PM6 spectrophotometer.

Example 7

Activation of PCPA in Human Serum with Clostripain

Approximately 3 mg (500 units) of lyophilized clostripain was dissolved in 1 ml of 10 mM Tris buffer (pH 8.0) along with $CaCl_2$ and Cleland's Reagent at final concentrations of 20 mM and 1 mM, respectively. This mixture was incubated at room temperature for approximately 2 hours. This solution was then added to serum in concentrations ranging from approximately 50 to 500 units of clostripain/ml of serum. One unit was defined as the amount of clostripain which could cleave one micromole of Nα-benzoyl arginine ethyl ester (BAEE) in one minute. Determination of PCPA levels in blood donor samples was performed with 250 units of clostripain per ml serum. The standard serum volume was 0.013 ml serum per ml total solution. This mixture was incubated for five minutes at 37° C., after which time Ellman's Reagent was added at the standard concentration to eliminate clostripain as it quickly derivatizes all sulfhydryl groups in the mixture. From this point, the standard assay as described in Example 2 was followed.

What is claimed is:

1. A method of enhancing sensitivity and specificity of an assay measuring enzymatic activity of carboxypeptidase A in a biological sample comprising:

(a) contacting the biological sample and a blank sample with a carboxypeptidase A substrate wherein said blank sample contains a specific inhibitor of carboxypeptidase A activity; and (b) measuring changes in optical density resulting from the hydrolysis of the carboxypeptidase A substrate by carboxypeptidase A in the biological fluid and in the blank sample, wherein the presence of the specific inhibitor of carboxypeptidase A in said blank sample enhances the sensitivity and specificity of the assay.

2. A method of measuring carboxypeptidase A levels in a biological fluid sample comprising:

contacting a biological fluid sample and a blank sample with a carboxypeptidase A substrate wherein said blank sample contains a specific inhibitor of carboxypeptidase A activity; and (b) measuring changes in optical density resulting from the hydrolysis of the carboxypeptidase A substrate by carboxypeptidase A in the biological fluid sample.

3. A method of diagnosing acute pancreatitis in a patient suspected of suffering from acute pancreatitis comprising:

(a) measuring carboxypeptidase A levels in a biological fluid sample from a patient and in a blank sample containing a specific inhibitor of carboxypeptidase A activity and detecting changes in optical density resulting from hydrolysis of a carboxypeptidase A substrate by any carboxypeptidase A in the biological fluid sample and in the blank sample; and (b) after subtracting the level of carboxypeptidase A activity determined in the blank sample from the levels determined in the biological sample, determining whether the measured levels of carboxypeptidase A in the biological fluid sample of the patient are elevated over levels in biological fluid samples from a healthy control population.

* * * * *